(12) United States Patent
Laux

(10) Patent No.: US 6,431,862 B1
(45) Date of Patent: Aug. 13, 2002

(54) CONNECTING PIN AND SOCKET CONNECTION FOR FASTENING DENTAL CROWN OR JAW SEGMENTS

(76) Inventor: Robert Laux, An der Steige 22, D-73462 Welzheim-Eselshalden (DE)

( * ) Notice: Subject to any disclaimer, the term of this patent is extended or adjusted under 35 U.S.C. 154(b) by 0 days.

(21) Appl. No.: 09/530,995

(22) PCT Filed: Nov. 5, 1998

(86) PCT No.: PCT/EP98/07049

§ 371 (c)(1),
(2), (4) Date: Jun. 30, 2000

(87) PCT Pub. No.: WO99/23972

PCT Pub. Date: May 20, 1999

(30) Foreign Application Priority Data

Nov. 9, 1997 (DE) .......................... 297 19 844
Nov. 23, 1997 (DE) .......................... 197 51 793
Mar. 10, 1998 (DE) .......................... 198 10 083

(51) Int. Cl.$^7$ ................................................ A61C 19/00
(52) U.S. Cl. .............................................. 433/74; 433/53
(58) Field of Search ........................... 433/74, 53, 220, 433/221

(56) References Cited

U.S. PATENT DOCUMENTS 1,140,539 A * 5/1915 Skinner ...................... 433/220
4,205,443 A * 6/1980 Weissman ................... 433/74
5,738,518 A * 4/1998 Nowak ........................ 433/74

FOREIGN PATENT DOCUMENTS

| DE | 31 08 700 | 9/1982 |
| DE | 33 01 617 | 7/1984 |
| DE | 196 00 854 | 9/1986 |
| DE | 38 07 591 | 9/1989 |

* cited by examiner

Primary Examiner—John J. Wilson
(74) Attorney, Agent, or Firm—Crowell & Moring LLP

(57) ABSTRACT

A connecting pin for a socket connection for fastening dental crown or jaw segments to a model base comprises a fixing shank and a socket shank. The socket shank can be inserted releasably into a seat in a guiding sleeve which is accommodated in the model base. In order to make available a connection which is inexpensive and easy to produce, the outer radial surface area of the fixing shank, not loaded by external forces, has a radial undercut at least in the area of the smallest radius ($r_{min}$) of the surface area as viewed along the length of the fixing shank.

8 Claims, 2 Drawing Sheets

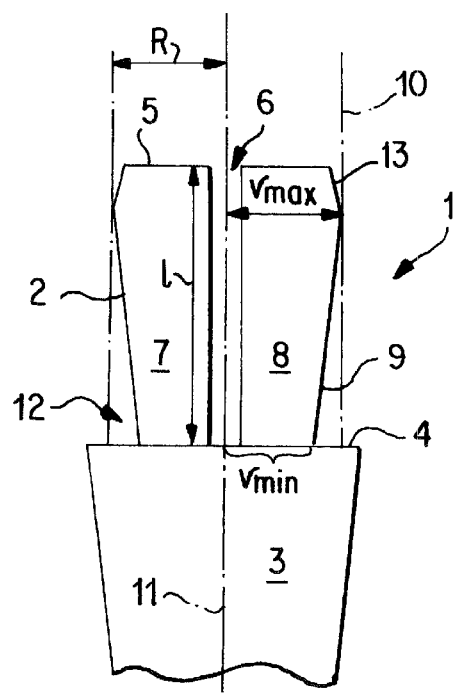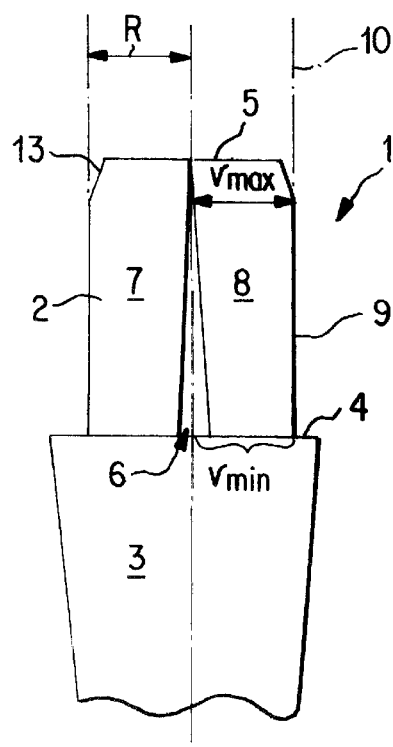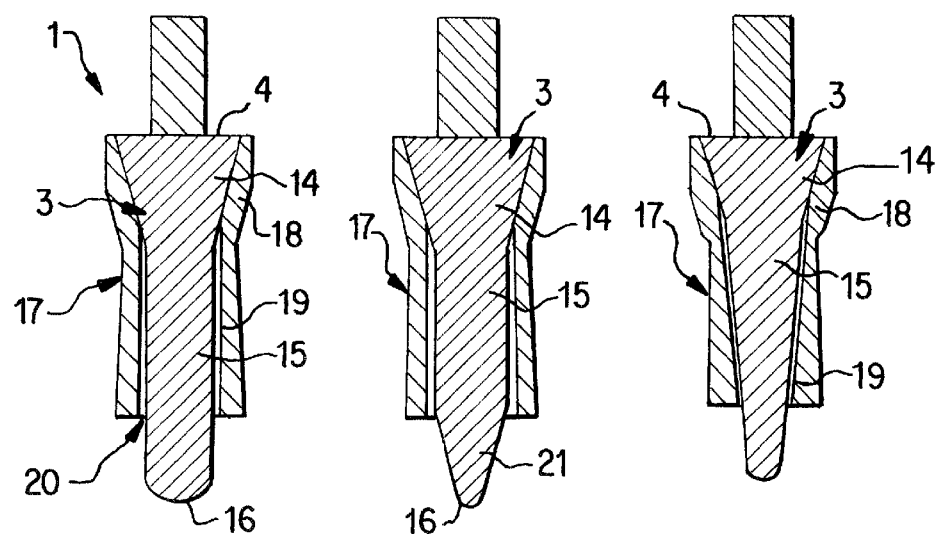
Fig. 1  Fig. 2
Fig. 3  Fig. 4  Fig. 5

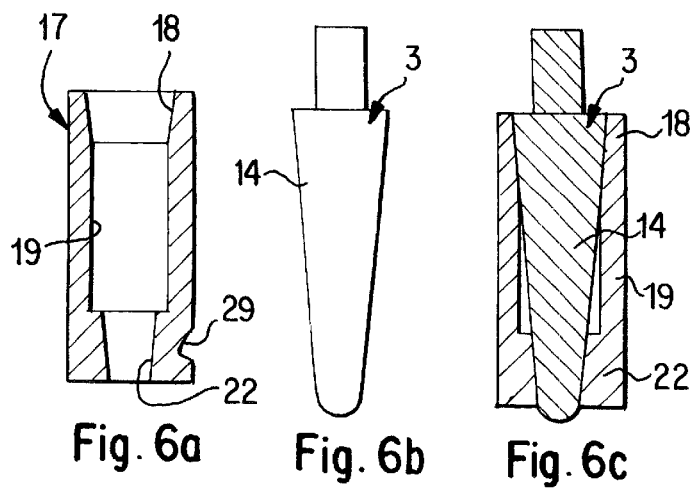
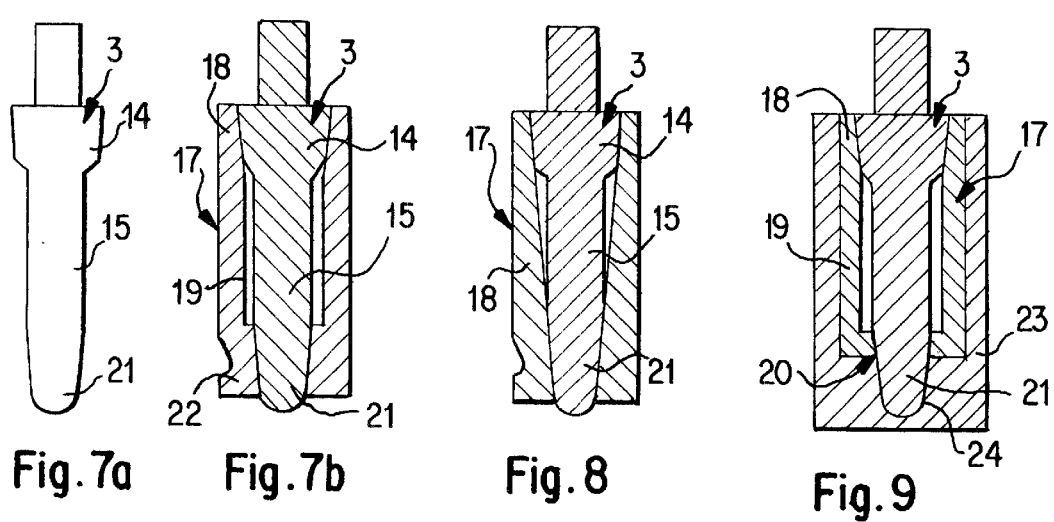
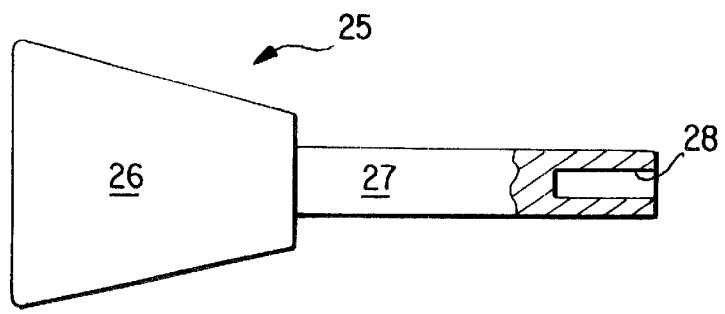

CONNECTING PIN AND SOCKET CONNECTION FOR FASTENING DENTAL CROWN OR JAW SEGMENTS

BACKGROUND OF THE INVENTION

The invention relates to a connecting pin for fastening dental crown or jaw segments.

Printed publication DE 3,807,591 C2 discloses a socket connection for connecting work models of individual dental crown or jaw segments to a model base. The socket connection comprises a connecting pin and a guiding sleeve which is rigidly connected to the model base. The connecting pin bearing the work models of the segments is releasably inserted into the guiding sleeve in the model base, as a result of which the work models are held securely on the model base for precision-working; in addition, the individual segments can be removed again at any time from the model base.

The connecting pin consists of two shanks, namely a fixing shank for permanent fixing in the underside of an individual tooth or jaw segment and a socket shank for releasable mounting in the guiding sleeve inserted into the model base. The fixing shank is inserted into a cylindrical hole which has been bored in the hardened plaster of the work model of the tooth or jaw segment, and it is connected permanently to the model by means of adhesive. The surface area of the fixing shank has circular grooves which provide for additional strengthening of the join between connecting pin and model.

A problem in this regard is that, on the one hand, the fixing shank and the borehole in the model have to be produced with the least possible tolerance and with little play, so as to ensure the greatest possible precision for working the model. On the other hand, because of this production free of play, there is a risk that the fixing shank, upon introduction into the borehole in the model, will tilt so that the axes of fixing shank and borehole are no longer parallel and, on account of the inclined position of insertion of the fixing shank, the model will not be held in the intended manner relative to the model base. Moreover, the obliquely inserted fixing shank cannot be sunk completely into the borehole, with the result that adjacent dental crown or jaw segments are placed slightly offset in height in the model base, which negatively affects the working precision of the model.

A further problem lies in the nature of the connection between the socket shank of the connecting pin and the guiding sleeve in the model base. The socket shank comprises two sections, of which at least one is of cylindrical design and is fitted releasably into the guiding sleeve of complementary shape. Between the cylindrical surface area of the socket shank and the cylindrical inner surface of the guiding sleeve, high static friction forces arise on account of the large friction surfaces, and these forces have to be overcome when removing a segment. If, after completion of the model work, the connecting pin is to be removed from the guiding sleeve, the work model may be damaged when releasing the socket shank from the sleeve, for example there may be undesired detachment of the connecting pin from the permanent fixture in the borehole of the model. The model base, too, may be damaged by the high release forces which are required for removing the work model.

Comparable socket connections are also disclosed by printed publications DE 3,301,617 A1 and DE 3,108,700 A1.

Furthermore, it is known from DE 196 00 854 to introduce a longitudinal slot into the fixing shank of the connecting pin in order to permit an elastic compression of the shank parts for easier insertion of the fixing shank into the work model. After insertion, the shank parts tend radially outward and generate a clamping force which fixes the connecting pin and by means of which the connecting pin is held securely in the work model.

SUMMARY OF THE INVENTION

The invention is based on the problem of making available a connection, which is inexpensive and easy to produce, between a model base and a work model of a dental crown or jaw segment, which connection permits precision-working of a dental work model and can be easily removed again.

According to the invention, this problem is achieved by running the shape of the surface area of the fixing shank to be connected to the work model. As the surface area of the fixing shank, not loaded by external forces, deviates from the cylinder shape and as the surface area in the region of the smallest radius is radially set back relative to the cylinder shape, an undercut is formed in the radial direction. When there are no external forces applied on the fixing shank, the shank parts in the unloaded state tend to run slightly radially outward from their attachment foot; the undercut is here defined as the difference between the maximum radius and the minimum radius of the fixing shank surface area in the unloaded state. The slot extends with a defined slot thickness between the shank parts, said shank parts being designed to be flexible at least to the extent that the shank parts in the area of the free end face of the fixing shank can be compressed for insertion into the borehole in the work model.

As a result of the compression of the shank parts, the surface area of the fixing shank changes and is now approximately cylindrical. Because of the elasticity and inherent stress, the compressed shank parts press radially outward. The surface area is approximately cylindrical, which means that, with a connecting pin fitted into the borehole of the work model, a surface pressure is exerted on the inner wall of the borehole, and this surface pressure is approximately uniform along the axial length of the fixing shank. This results in high static friction forces which securely clamp the fixing shank in the borehole, but which are distributed uniformly over the inner surface of the borehole so that force peaks exerting a load on the borehole are avoided. In addition, insertion into the borehole is made easier because the diameter of the fixing shank, with the shank parts compressed, is approximately the same as or slightly smaller than the diameter of the borehole, so that there is only minimal friction to be overcome upon insertion. The diameter of the cylindrical surface area here corresponds to the diameter of the unloaded fixing shank in the area of the smallest radius.

The undercut of the unloaded fixing shank, in combination with the slot formed between the shank parts, ensures that the shank parts can be compressed until a cylindrical surface area of the fixing shank is obtained.

Attainment of the cylinder shape is preferably assisted by the fact that the distance between the shank parts in the area of the free end face of the fixing shank—the slot thickness in this area—is at least as great as the sum of the two radially opposite undercuts in the area of the attachment foot of the shank parts or in the area of a support shoulder which is advantageously formed at the transition between fixing shank and socket shank. The undercuts measured in the radial direction are leveled out by the compression, in which respect, with uniform pressure on the fixing shank, each shank part levels out its radial undercut until the surface area of the fixing shank assumes a cylinder shape.

The fixing shank can be designed with a uniform slot thickness which results in a non-uniform thickness of the shank parts, as viewed along the axial length, so that an undercut is formed at the foot of the shank parts. However, it may also be expedient to design the shank parts uniformly and to provide the slot with a varying slot thickness.

In one advantageous embodiment, between the socket shank of the connecting pin, projecting into the guiding sleeve, and the guiding sleeve itself there is at least one cone-shaped connecting section whose surface cooperates with the outer surface area of the socket shank and with the inner surface of the guiding sleeve, the axial length of the connecting section being at most half the length of the socket shank. The connecting section is used for guiding the connecting pin in the sleeve, and in this section the contacting surfaces of the socket shank and of the sleeve are of complementary design and lie against one another with static friction. Adjoining the conical connecting section there is a further section, and in this section the radially facing surfaces of socket shank and sleeve are either of non-complementary design or have concentric, spaced-apart surface areas, so that in any case the inner surface in the guiding sleeve and the outer surface area of the socket shank lie at a distance from one another and are therefore free from friction. This ensures that the friction surface can be essentially limited only to the first conically shaped section of reduced length. The frictional forces, in particular static friction forces, are reduced to such an extent that, in order to release the socket connection, it is necessary to apply only slight reaction forces which do not damage the work model. The frictional forces should in particular not exceed those holding forces with which the fixing shank is held in the borehole of the work model. At the same time, however, the holding forces of the connection are sufficient to exclude the possibility of play developing. The connection is able to take up, without movement, the forces which normally occur in model working.

It may be expedient to extend the axial length of the conical connecting section to as much as two thirds of the axial length of the socket shank.

The limited length of the conical section also makes it possible, in a preferred development, to provide the socket shank with a second conical connecting section which is arranged at an axial distance from the first conical connecting section and to which there is assigned a section of once again complementary shape in the guiding sleeve. Provided between the two connecting sections, there is a middle section which performs no connecting function. In the area of this middle section, which is preferably of cylindrical design, the socket shank and the guiding sleeve are of non-complementary design or lie at a distance from one another, in particular without any contact between the surface area of the socket shank and the inner surface of the guiding sleeve.

In a preferred embodiment, the socket shank is provided with three sections in the order of conical section/cylindrical section/conical section, where the conical sections assume the function of connecting sections, to which there are assigned sections of complementary shape in the guiding sleeve, while the cylindrical section by contrast is arranged at a distance from the inner surface of the guiding sleeve. In this embodiment, the total axial length of the socket shank can be used for the connection to the guiding sleeve, the first conical section being arranged adjoining the support shoulder of the connecting pin, and the second conical section being arranged in the area of the free end face of the socket shank, so that the pin is guided in the sleeve at both axially opposite ends of the socket shank. The long guide ensures an optimum seat in the sleeve, and the reduced connecting surfaces ensure easy release of the connection.

The axial length of all the conical sections taken together is preferably at most two thirds, particularly at most half, of the length of the socket shank.

BRIEF DESCRIPTION OF THE DRAWINGS

Further advantages and preferred embodiments will become apparent from the attached claims, the description of the figures and the drawings. In these drawings:

FIG. 1 shows a view of a fixing shank of a connecting pin in the expanded position, FIG. 2 shows the fixing shank from FIG. 1 with the shank parts compressed, FIGS. 3 though 9 show various embodiments of a connecting pin with a socket shank inserted into a guiding sleeve, and FIG. 10 shows a hand tool for easier handling of a connecting pin.

DETAILED DESCRIPTION OF THE DRAWINGS

In FIG. 1, the upper part of a connecting pin 1 is represented, which connecting pin is used for socket connections for fastening dental crown or jaw segments of plaster or the like on a model base which is likewise usually made of plaster. The connecting pin 1 consists of two axially adjoining shanks, namely a fixing shank 2 which is fitted into a prepared borehole of a dental crown or jaw segment and adhesively bonded thereto, and a socket shank 3 which is fitted releasably in a guiding sleeve which is cast into the model base, and whose upper conical section can be seen in FIG. 1. The material usually chosen for the connecting pin is metal, while the materials usually chosen for the guiding sleeve are metal or plastic.

In an alternative embodiment, the fixing shank 2 is fitted into the borehole in the segment without adhesive bonding.

The fixing shank 2 with the axial length 1 consists of two shank parts 7, 8 between which a slot 6 is formed. Formed in the foot area of the shank parts 7, 8, the transition area between the fixing shank 2 and the socket shank 3, there is a support shoulder 4 which ensures that the connecting pin is fitted with a defined length into the borehole in the tooth or jaw model. The support shoulder 4 is formed by the two shank parts 7, 8 being set back radially inward at the transition between socket shank and fixing shank in relation to the maximum radius of the socket shank 3.

In FIG. 1, the fixing shank 2 is represented in the unloaded state, free from external forces. The slot 6 extending along the axial length 1 between the two shank parts 7, 8 has a constant slot thickness. The surface area 9 of the two shank parts 7, 8 is of approximately cone-shaped design, with a minimum radius $r_{min}$ in the area of the support shoulder 4 and a maximum radius $r_{max}$ which is obtained by means of a chamfer 13 just under the free end face 5 of the fixing shank 2, the radii $r_{min}$, $r_{max}$ being measured in relation to the longitudinal axis 11 of the connecting pin. In relation to a cylindrical envelope 10, which is guided through the radial outer points of the surface area 9 of the shank parts 7, 8 with radius $r_{max}$ and which has the radius R identical to $r_{max}$, the surface area 9 forms a radial undercut 12 in the area of the support shoulder 4. This undercut 12 can be defined as the difference $r_{max}-r_{min}$ between maximum and minimum radius of the surface area and, in the illustrative embodiment, represents the extent by which the attachment foot of the shank parts 7, 8 is set back radially inward in relation to the radially outermost points of the surface area 9.

In the illustrative embodiment, the surface area 9 of the unloaded fixing shank 2 has an approximately conical shape; with at the same time a slot thickness remaining constant along the length 1 of the shank 2, this has the result that the shank parts 7, 8 have a radial thickness which increases in the direction toward the free end face 5.

However, it may also be expedient in some cases to provide the shank parts with a constant thickness, so that, with a conical surface area, a slot thickness is obtained which increases in the direction toward the free end face of the fixing shank. According to a further embodiment, the shank parts and also the slot have a thickness which changes along the axial length.

In FIG. 2, the fixing shank 2 of the connecting pin 1 is represented with the shank parts 7, 8 pressed radially inward, said shank parts 7, 8 touching each other in the area of the free end face 5. If the spacing of the unloaded shank parts 7, 8 is expediently chosen such that the slot thickness in the area of the free end face 5 is approximately the same size as the sum of the two undercuts 12 on radially opposite sides of each shank part 7, 8, then the surface area 9 of the compressed shank parts 7, 8 assumes an approximately cylindrical shape; the minimum radius $r_{min}$, the maximum radius $r_{max}$ and the radius R of the envelope 10 are approximately the same size, so that the surface area 9 essentially coincides with the cylindrical envelope 10. The shank parts 7, 8 compressed to form a cylinder can be inserted with minimal effort into a cylindrical borehole. The chamfer 13 prevents tilting of the fixing shank during insertion.

In the illustrative embodiment, the shank parts 7, 8 are set back radially inward on the support shoulder 4. However, it may also be expedient to arrange the shank parts in such a way that the surface area of the fixing shank merges directly into the surface area of the socket shank; in this design, the connecting pin has no support shoulder.

It is possible to have two shank parts or more than two shank parts. In the case of four shank parts, the two slots between the shank parts preferably form a 90° angle. The fixing shank is preferably designed to be mirror-symmetrical in relation to a mirror plane which includes the longitudinal axis of the connecting pin.

FIGS. 3 through 9 show different embodiments of socket connections each consisting of a connecting pin in a guiding sleeve.

According to FIG. 3, the socket shank 3 of the connecting pin 1 consists of two sections, namely a cone-shaped connecting section 14 immediately adjacent to the support shoulder 4, and an adjoining cylindrical section 15 whose free end face 16 is rounded off in a partial sphere shape. The diameter of the cylindrical section 15 is the same size as the minimum diameter of the connecting section 14. The length of the socket shank 3 exceeds the length of the guiding sleeve 17 which has a through-opening in the base through which the cylindrical section 15 of the socket shank 3 protrudes. The length of the cone-shaped connecting section 14 is approximately half as long as the length of the cylindrical section 15; the overall length of the connecting section 14 is approximately one third of the axial length of the socket shank 3. The cone angle of the connecting section 14 is greater than one degree. The choice of cone angle can be used to influence the frictional forces with which the socket connection is held together, with a smaller cone angle resulting in greater static friction and a larger cone angle resulting in less static friction. If the guiding sleeve is made of metal, the cone angle is preferably four degrees, or, in the case of a plastic sleeve, the cone angle is preferably six degrees.

The guiding sleeve 17 has two sections 18, 19 corresponding to the two sections 14, 15 of the socket shank 3. The first section 18 of the guiding sleeve 17 has an inner cone which is designed to match the conical connecting section 14, so that, when the connecting pin 1 is inserted, the surface area of the connecting section 14 lies directly on the inner surface of the first section 18 of the guiding sleeve 17. The connecting section 14 of the socket shank 3 and the corresponding section 18 of the guiding sleeve finish flush with each other in the area of the support shoulder 4.

The second section 19 of the guiding sleeve 17 is shaped cylindrically like the corresponding section 15 of the socket shank 3, but it has a greater diameter than the socket shank, so that the surface area of the socket shank and the inner surface of the guiding sleeve lie spaced apart in this area, without contact and without friction.

The diameter of the through-opening 20 in the base of the second section 19 of the guiding sleeve 17 is slightly greater than the cylindrical section 15 of the socket shank 3. Thus, although the connecting section is not guided in the area of the through-opening, plaster is prevented from penetrating into the guiding sleeve 17. Further guiding or stabilizing is obtained by means of the section of the socket shank protruding axially from the guiding sleeve, which section is inserted into the plaster of the model base.

The socket connection represented in FIG. 4 has a modified connecting pin compared to the illustrative embodiment in FIG. 3. The socket shank 3 consists of three sections 14, 15 and 21, where the first two sections 14, 15 are cone-shaped and cylindrical and the third section 21 adjacent to the free end face 16 is in turn cone-shaped. The cone angles of the two conical sections can be identical or different. The second, cylindrical section 15 lies radially at a distance from the corresponding section of the guiding sleeve. The third, cone-shaped section 21 protrudes fully from the guiding sleeve 17. The axial length of the two conical sections 14 and 21 taken together amounts to a maximum of two thirds of the axial length of the socket shank 3.

In the illustrative embodiment according to FIG. 5, the socket shank 3 of the connecting pin consists of a total of two sections 14, 15 which both have a cone shape. The cone angle of the connecting section 14 adjacent to the support shoulder 4 is greater than the cone angle of the contiguous second section 15. The first section 18 of the guiding sleeve 17 is designed to match the connecting section 14, the surface area of the connecting section 14 bearing on the inner surface of the section 18. The inner surface of the second section 19 of the guiding sleeve 17 is at a constant distance from the surface area of the corresponding second section 15 of the socket shank 3.

A feature which the illustrative embodiments according to FIGS. 3 through 5 have in common is that the connecting pin obtains further support from that section lying adjacent to the free end face, protruding from the guiding sleeve and inserted directly into the material of the model base.

FIGS. 6a through 6c show a guiding sleeve and a connecting pin separately and in the assembled position. According to FIG. 6a, the guiding sleeve 17 consists of three axially succeeding sections 18, 19 and 22, the axially outer sections 18 and 22 being conical and having the same cone angle, and the intermediate section 19 being cylindrical. By choosing the same cone angles for the conical sections 18, 22, production is made easier because the cone can be made in one work operation. Provided on the outer surface area of the guiding sleeve 17, there is a retention 29 by means of which the join between guiding sleeve and model base is strengthened.

The socket shank 3 of the pin represented in FIG. 6b has a conical section 14 whose cone angle is adapted to that of the conical sections of the guiding sleeve.

When the connecting pin is inserted, the upper and lower areas of the section 14 of the socket shank 3 according to FIG. 6c are received in the corresponding conical sections 18 and 22 of the guiding sleeve. The middle section 19 of the guiding sleeve is not designed matching the section 14 of the socket shank 3, so that in this section the outer surface area of the section 14 and the inner surface of the section 19 lie at a distance from one another. In this design, the section 14 of the socket shank 3 is, with a uniform surface area, divided into three sub-sections, of which the two outer ones make the connection to the guiding sleeve.

FIGS. 7a and 7b show a further illustrative embodiment. The socket shank 3 of the connecting pin consists of two axially outer conical sections 14 and 21 and an intermediate cylindrical section 15. The associated guiding sleeve, like the guiding sleeve shown in FIGS. 6a and 6c, consists of two conical sections 18, 22 and an intermediate cylindrical section 19 whose diameter, however, is greater than the corresponding cylindrical section 15 of the socket shank 3.

FIG. 8 shows a further illustrative embodiment in which the socket shank 3 of the connecting pin is identical to the socket shank shown in FIGS. 7a and 7b and has two conical sections 14, 21 and a middle cylindrical section 15. The guiding sleeve 17 is provided with a section 18 shaped as an inner cone and continuing along its axial length, the cone angle of which section 18 corresponds to that of the two cone sections 14, 21 of the connecting pin.

According to FIG. 9, the socket shank 3 has the same construction as in the illustrative embodiment in FIG. 8. The guiding sleeve 17 has an upper conical section 18 and a lower cylindrical section 19. A model base 23 is also represented, into which the guiding sleeve 17 is fitted. The model base 23 has a recess 24 immediately adjacent to the through-opening 20 in the base of the guiding sleeve 17; the recess 24 receives the section 21 of the socket shank 3.

FIG. 10 shows a hand tool 25 making it easier to pick up and set down a connecting pin. The hand tool consists of a grip part 26 to which a rod 27 is attached, at the free end face of which there is introduced a receiving bore 28. To make it easier to handle a connecting pin, the latter can be accommodated in the receiving bore and fitted into the borehole of the model.

LIST OF REFERENCE NUMBERS

1 Connecting pin
2 Fixing shank
3 Socket shank
4 Support shoulder
5 End face
6 Slot
7 Shank part
8 Shank part
9 Surface area
10 Envelope
11 Longitudinal axis
12 Undercut
13 Chamfer
14 Connecting section
15 Section
16 End face
17 Guiding sleeve
18 Section
19 Section
20 Through-opening
21 Section
22 Section
23 Model base
24 Recess
25 Hand tool
26 Grip part
27 Rod
28 Receiving bore
29 Retention

What is claimed is:

1. A connection pin for a socket connection for fastening dental crown or jaw segments to a model base, with a fixing shank and a socket shank, which socket shank can be inserted releasably into a seat in a guiding sleeve which is accommodated in the model base, the fixing shank having a slot running in the longitudinal direction of the connecting pin and extending over the axial length of the fixing shank, which slot divides the fixing shank into at least two spaced-apart, flexible shank parts, and the radially outer surface area of the fixing shank, not loaded by external forces, having a variable radius as viewed along the length of the fixing shank, wherein the surface area of the fixing shank, not loaded by the external forces, runs approximately conically, and the surface area, in relation to a cylindrical envelope whose radius corresponds to the maximum radial distance of the surface area from the longitudinal axis, forms a radial undercut at least in the area of the smallest radius of the surface area, and the surface area of the fixing shank being configured to be reduced by compression to a cylindrical shape so as to be insertable into a cylindrical borehead comprising the seat of the guiding sleeve, wherein the slot thickness in the area of the free-end face of the fixing shank is greater than, or equal to, the sum of radially opposite undercuts in the area of the smallest radius of the surface area.

2. The connecting pin according to claim 1, wherein a support shoulder is formed in the transition area between fixing shank and socket shank, and the slot extends between the free-end face of the fixing shank and the support shoulder.

3. The connecting pin according to claim 1, wherein the slot has a uniform slot thickness over the length of the fixing shank.

4. The connecting pin according to claim 1, wherein the shank parts have an approximately uniform thickness over the length of the fixing shank.

5. The connecting pin according to claim 1, wherein the fixing shank has a total of two slots which are arranged at a 90° angle to each other.

6. The connecting pin according to claim 1, wherein the fixing shank is chamfered in the area of its free-end face.

7. The connecting pin according to claim 1, wherein the fixing shank is made mirror-symmetrical.

8. The connecting pin according to claim 1, wherein a hand tool is provided making it easier to pick up and set down the connecting pin, the hand tool having a grip part and a rod, at the free-end face of which there is introduced a receiving bore for receiving the connecting pin.

* * * * *